(12) United States Patent
Klein et al.

(10) Patent No.: US 6,899,894 B1
(45) Date of Patent: May 31, 2005

(54) TRANSDERMAL THERAPEUTIC SYSTEM CONTAINING HORMONES AND CRYSTALLIZATION INHIBITORS

(75) Inventors: Robert Klein, Neuwied (DE); Reinhold Meconi, Neuwied (DE); Walter Müller, Neuwied (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 09/720,287

(22) PCT Filed: Jun. 8, 1999

(86) PCT No.: PCT/EP99/03922

§ 371 (c)(1),
(2), (4) Date: May 10, 2001

(87) PCT Pub. No.: WO99/66901

PCT Pub. Date: Dec. 29, 1999

(30) Foreign Application Priority Data

Jun. 25, 1998 (DE) .......................... 198 28 273

(51) Int. Cl.$^7$ .......................... A61F 13/02; A61L 15/16
(52) U.S. Cl. ...................... 424/448; 424/449
(58) Field of Search ................. 424/448, 449, 424/443, 484, 489

(56) References Cited

U.S. PATENT DOCUMENTS

| | | | | |
|---|---|---|---|---|
| 4,954,343 A | * | 9/1990 | Hosaka et al. | 424/448 |
| 5,352,457 A | * | 10/1994 | Jenkins | 424/448 |
| 5,357,004 A | * | 10/1994 | Calton et al. | 525/435 |
| 5,393,529 A | * | 2/1995 | Hoffmann et al. | 424/445 |
| 5,662,923 A | * | 9/1997 | Rorger | 424/445 |
| 5,676,968 A | * | 10/1997 | Lipp et al. | 424/448 |
| 5,683,711 A | * | 11/1997 | Fischer et al. | 424/449 |
| 5,730,999 A | * | 3/1998 | Lehmann et al. | 424/443 |
| 5,744,162 A | * | 4/1998 | Okabe et al. | 424/448 |
| 5,906,830 A | * | 5/1999 | Farinas et al. | 424/448 |
| 5,951,999 A | * | 9/1999 | Therriault et al. | 424/448 |
| 6,153,216 A | * | 11/2000 | Cordes et al. | 424/448 |
| 6,238,284 B1 | * | 5/2001 | Dittgen et al. | 156/283 |

FOREIGN PATENT DOCUMENTS

| | | | |
|---|---|---|---|
| DE | 37 43 946 A 1 | 3/1987 | |
| DE | 43 36 557 A1 | 11/1994 | |
| DE | 43 36 557 A 1 | 11/1994 | |
| DE | 43 33 595 A1 | 4/1995 | |
| DE | 197 28 517 A1 | 1/1999 | |
| EP | 0 421 454 A2 | 4/1991 | |
| EP | 0 531 938 A1 | 3/1993 | |
| WO | WO 93/00058 | 1/1993 | |
| WO | WO 95/09618 | 4/1995 | |
| WO | WO 95/22322 | 8/1995 | |
| WO | WO 95/30409 | 11/1995 | |
| WO | WO 9723227 A1 | * 7/1997 | A61K/31/565 |

* cited by examiner

Primary Examiner—Thurman K. Page
Assistant Examiner—Isis Ghali
(74) Attorney, Agent, or Firm—D. Peter Hochberg; Sean Mellino; Katherine R. Vieyra

(57) ABSTRACT

A transdermal therapeutic system in plaster form for controlled release of oestradiol in combination with norethisterone acetate, comprising a backing layer, a reservoir supersaturated with active ingredients which is attached to said backing layer and prepared using polyacrylate pressure-sensitive adhesives and crystallization inhibitors, and a detachable protective layer, is characterized in that the crystallization inhibitor is an amino-containing polymer.

13 Claims, No Drawings

TRANSDERMAL THERAPEUTIC SYSTEM CONTAINING HORMONES AND CRYSTALLIZATION INHIBITORS

CROSS-REFERENCE TO RELATED APPLICATIONS

This application is a Section 371 National Stage application of International Application No. PCT/EP99/03922, filed on Jun. 8, 1999, which claims priority of German Application No. 198 28 273.7, filed Jun. 25, 1998.

BACKGROUND OF THE INVENTION

1. Field of the Invention

The invention relates to a transdermal therapeutic system (TTS) for controlled release of oestradiol in combination with norethisterone acetate to the human skin.

2. Description of the Prior Art

Oestradiol in combination with norethisterone acetate has a very low saturation solubility in the auxiliaries normally used to formulate transdermal therapeutic systems, such as polyacrylate adhesives, tackifiers, plasticizers and absorption improvers. As a result, the capacity to load a TTS with dissolved active ingredient is greatly limited, and/or, in the case of supersaturation, unwanted crystallization occurs during storage. Consequently, the proportion of dissolved active ingredients in the matrix is reduced, which has an adverse effect on their release.

For combined preparations comprising oestradiol and norethisterone acetate, administration forms have been developed in which the active ingredients in a transdermal therapeutic system are contained in separate areas. However, manufacturing such TTSs is very expensive.

Accommodating drying agents together with transdermal therapeutic systems in the primary packaging reduces the risk of recrystallization but is far from straightforward.

DE-A 43 36 557 describes an active substance transdermal therapeutic system based on a pressure-sensitive adhesive which comprises rosin esters. It is prepared by kneading the components in the melt at temperatures between 100 and 140° C. and then carrying out coating. Such high temperatures in the preparation of pharmaceutical forms carry with them the risk that degradation products may be formed in an unacceptably high amount.

WO 95/30409 describes a topical polymer release system for the administration of certain active ingredients by means of a propellantless aerosol pump. The absence of adhesives is emphasized as an advantage. Additional components used include crystallization inhibitors/stabilizers and/or penetration enhancers such as substituted cyclodextrins, Transcutol, urea and isoterpenes; the active substance combination of oestradiol and norethisterone acetate is not claimed.

SUMMARY OF THE INVENTION

It is therefore an object of the invention to provide a stable, i.e. recrystallization-free, plaster comprising the active ingredients oestradiol and norethisterone acetate.

It has surprisingly been found that in a transdermal therapeutic system having the features of the main claim this object is achieved by the use of an amino-containing polymer as crystallization inhibitor. Advantageous crystallization inhibitors used are polymers based on butyl methacrylate, 2-dimethylaminoethyl methacrylate and methyl methacrylate, preferably in a molar ratio of 1:2:1, polyaminoamides, polyaminoimidazolines, polyetherurethaneamines, polyamines and polyglucosamines.

It has been found that the crystallization inhibitors are particularly suitable in a proportion of from 0.05 to 30% by weight.

The formation of hydrogen bonds between the basic groups of the crystallization inhibitor and the mobile hydrogen atoms of the oestradiol molecule results in immobilization of oestradiol. Consequently, the concentration of freely mobile oestradiol in the matrix is reduced and crystallization prevented.

The pressure-sensitive adhesive reservoir contains oestradiol and norethisterone acetate in a weight ratio of from 1:2 to 1:15, preferably from 1:3 to 1:7, and in an overall concentration of up to 25% by weight.

The reservoir may comprise a constituent from the group consisting of ageing inhibitors, plasticizers, antioxidants and absorption improvers, the plasticizer being used in a concentration of from 0 to 5% by weight and the ageing inhibitor in a concentration of from 0.1 to 2% by weight.

Suitable ageing inhibitors, plasticizers, antioxidants and absorption improvers are known to the person skilled in the art and are described, for example, in DE 37 43 946.

In order to be able to apply the transdermal therapeutic system to the skin it is necessary for the system to have pressure-sensitive adhesive properties. In order to impart these properties to the transdermal therapeutic system of the invention use is made of polyacrylate pressure-sensitive adhesives in the form of solutions in organic solvents, known as solvent-based pressure-sensitive adhesives.

It is also possible to use polyacrylate pressure-sensitive adhesives in the form of aqueous dispersions.

Also suitable are hot-melt pressure-sensitive adhesives. These are free of solvent or dispersant and are applied from the melt.

UV-crosslinkable acrylate pressure-sensitive adhesives are also suitable. These are solvent-free and are applied using the conventional coating techniques. Subsequently, the polymer chains are crosslinked by irradiation with UV light. This is necessary in order to give the pressure-sensitive adhesive adequate cohesion.

The reservoir of the transdermal therapeutic system may consist of a plurality of layers each with the same or different concentrations of active ingredient.

The layer thickness of the reservoir is from 0.02 mm to 0.500 mm but preferably from 0.030 mm to 0.200 mm.

The reservoir can be provided with an additional pressure-sensitive adhesive layer and/or with a pressure-sensitive adhesive margin. This becomes necessary when the pressure-sensitive adhesive properties of the reservoir itself are inadequate.

The transdermal therapeutic system of the present invention is intended for therapeutic applications in human medicine.

DESCRIPTION OF THE PREFERRED EMBODIMENT

The invention is illustrated below on the basis of examples.

EXAMPLE 1

155.08 g of Durotak 387-2287 (National Starch) (polyacrylate pressure-sensitive adhesive (PSA)) and
4.81 g of Eudragit E 100 (Röhm) (polyacrylate) are homogenized with stirring and, together with a suspension of
2.17 g of Eutanol G (Caesar und Loretz) (long-chain fatty alcohol)

0.03 g of aluminium acetylacetonate (Merck-Schuchardt),
1.29 g of oestradiol hemihydrate and
8.33 g of norethisterone acetate, are dissolved in a solvent mixture comprising
27.98 g of ethyl acetate and
27.97 g of ethanol.

The resultant adhesive solution is applied to a detachable protective layer of Hostaphan RN 100, siliconized on both sides, to give after drying an active substance matrix having a coated weight of 96.3 g/m$^2$. A backing layer impermeable to the active ingredients (0.015 mm thick polyester film) is laminated onto the resultant matrix. Subsequently, TTS patches measuring 40 cm$_2$ are punched out.

EXAMPLES 2–7 AND COMPARISON

Preparation takes place as described under Example 1 but with the starting materials and amounts specified in Table 1.

TABLE 1

Composition (g)

| | | Example | | | | | |
|---|---|---|---|---|---|---|---|
| | Comparison | 2 | 3 | 4 | 5 | 6 | 7 |
| Durotak 387-2287 | 424.31 | 132.84 | 162.25 | 171.50 | 171.50 | 162.25 | 171.50 |
| Oestradiol hemihydrate | 3.37 | 1.34 | 1.34 | 1.34 | 1.34 | 1.34 | 1.34 |
| Norethisterone acetate | 21.60 | 8.65 | 8.65 | 8.65 | 8.65 | 8.65 | 8.65 |
| Eutanol G | 5.59 | 2.25 | 2.25 | 2.25 | 2.25 | 2.25 | 2.25 |
| Al acetyl-acetonate | 1.36 | 0.054 | 0.054 | 0.054 | 0.054 | 0.054 | 0.054 |
| Ethyl acetate | — | 36.48 | 29.28 | 27.11 | 27.11 | 29.28 | 27.11 |
| Ethanol | — | 36.48 | 29.28 | 27.11 | 27.11 | 29.28 | 27.11 |
| Methyl ethyl ketone | 134.79 | — | — | — | — | — | — |
| EUREDUR 145 — A curing agent for epoxide resins | — | 20.0 | — | — | — | — | — |
| EUREDUR 125 — A curing agent for epoxide resins | — | — | 5.0 | — | — | — | — |
| EUREDUR 250 — A curing agent for epoxide resins | — | — | — | 0.5 | — | — | — |
| EUREDUR 43 — A curing agent for epoxide resins | — | — | — | — | 0.5 | — | — |
| EUREDUR 27 — A curing agent for epoxide resins | — | — | — | — | — | 5.0 | — |
| EUREDUR 10 — A curing agent for epoxide resins | — | — | — | — | — | — | 0.5 |

The test for signs of recrystallization was conducted microscopically in transmitted light at 40 times magnification. The results are set out in Table 2.

TABLE 2

| | Recrystallization |
|---|---|
| Example 1 | Crystals per 40 cm$^2$ following storage for 3 months at 40° C. |
| Comparison | 154 |
| 1 | 0 |
| 2 | 0 |
| 3 | 0 |

TABLE 2-continued

| | Recrystallization |
|---|---|
| Example 1 | Crystals per 40 cm$^2$ following storage for 3 months at 40° C. |
| 4 | 0 |
| 5 | 0 |
| 6 | 0 |
| 7 | 0 |

As evident from Table 2 the addition of crystallization inhibitors gives transdermal therapeutic systems which are free from crystallization, in contrast to the comparative example (without crystallization inhibitor) in which there is considerable crystallization within a period of 3 months.

The invention has been described with particular emphasis on the preferred embodiments, but variations and modifications within the spirit and scope of the invention may occur to those skilled in the art to which the invention pertains.

What is claimed is:

1. A transdermal therapeutic system in plaster form for controlled release of oestradiol in combination with norethisterone acetate, comprising:
   a backing layer;
   a reservoir supersaturated with active ingredients, said active ingredients being oestradiol and norethisterone acetate, said reservoir being attached to said backing layer and being prepared by mixing polyacrylate pressure-sensitive adhesives, crystallization inhibitor(s), and said active ingredients wherein the crystallization inhibitor(s) is amino group-containing polymer selected from the group consisting of polyaminoamides, polyaminoimidazolines, polyetherurethaneamines and polyglucosamines; and a detachable protective layer.

2. A transdermal therapeutic system according to claim 1, wherein the reservoir comprises at least one crystallization inhibitor in proportion of from 0.05 to 30% by weight.

3. A transdermal therapeutic system according to claim 1, wherein the reservoir comprises oestradiol and norethisterone acetate in a weight ratio of from 1:2 to 1:15, and in an overall concentration of up to 25% by weight.

4. A transdermal therapeutic system according to claim 1, wherein the reservoir includes a constituent from the group consisting of aging inhibitors, plasticizers, antioxidants and absorption improvers, the plasticizers being used in a concentration of 0 to 5% by weight and the aging inhibitor in a concentration of 0.1 to 2% by weight.

5. A transdermal therapeutic system according to claim 1, wherein the pressure-sensitive adhesive is selected from the group consisting of a solvent-based adhesive, a dispersion adhesive, a hot-melt adhesive and a UV-crosslinkable adhesive.

6. A transdermal therapeutic system according to claim 1, wherein the reservoir consists of at least two layers.

7. A transdermal therapeutic system according to claim 1, wherein the reservoir has a layer thickness of 0.02 mm to 0.500 mm.

8. A transdermal therapeutic system according to claim 1, wherein the reservoir is provided with an additional pressure-sensitive adhesive layer.

9. A transdermal therapeutic system according to claim 3, wherein the reservoir comprises oestradiol and norethisterone acetate in a weight ratio of from 1:3 to 1:7.

10. A transdermal therapeutic system according to claim 7, wherein the reservoir has a layer thickness of 0.030 to 0.200 mm.

11. A transdermal therapeutic system according to claim 8, wherein the reservoir is provided with a pressure-sensitive adhesive margin.

12. A transdermal therapeutic system according to claim 1, wherein the reservoir is provided with a pressure-sensitive adhesive margin.

13. A method for providing a transdermal therapeutic system for therapeutic applications of a drug comprising oestradiol in combination with norethisterone in human medicine, said method comprising:

applying said transdermal therapeutic system to the skin of a patient; and controlling the release of oestradiol in combination with norethisterone acetate to the human skin by providing a reservoir in said transdermal therapeutic system, said reservoir being supersaturated with the active ingredients, oestradiol and norethisterone acetate, and being attached to a backing layer, wherein said reservoir comprises at least one amino group-containing polymer as a crystallization inhibitor, and at least one adhesive consisting of a polyacrylate pressure-sensitive adhesives;

wherein said crystallization inhibitor is an amino group-containing polymer selected from the group consisting of polyaminoamides, polyaminoimidazolines, polyetherurethaneamines, and polyglucosamines and wherein hydrogen bonds are created between basic groups of said at least one amino group-containing crystallization inhibitor and the mobile hydrogen atom of the oestradiol to immobilize the oestradiol to reduce the concentration of freely mobile oestradiol in the matrix to prevent crystallization.

* * * * *